US006197323B1

(12) United States Patent
Georgieff

(10) Patent No.: US 6,197,323 B1
(45) Date of Patent: Mar. 6, 2001

(54) MEDICINAL PREPARATION CONTAINING A LIPOPHILIC INERT GAS

(76) Inventor: Michael Georgieff, Panoramastrasse 29, 89081 Ulm/Ermingen (DE)

(*) Notice: Subject to any disclaimer, the term of this patent is extended or adjusted under 35 U.S.C. 154(b) by 0 days.

(21) Appl. No.: 09/037,523

(22) Filed: Mar. 10, 1998

(30) Foreign Application Priority Data

Mar. 10, 1997 (DE) .............................................. 197 09 704
Aug. 8, 1997 (EP) .................................................. 97113757

(51) Int. Cl.⁷ ........................................................ A61F 2/02
(52) U.S. Cl. ........................... 424/423; 514/816; 514/937
(58) Field of Search ............................ 424/423; 514/816, 514/937

(56) References Cited

U.S. PATENT DOCUMENTS

| | | |
|---|---|---|
| 4,622,219 | 11/1986 | Haynes . |
| 4,725,442 | 2/1988 | Haynes . |
| 5,088,499 | 2/1992 | Unger . |
| 5,334,381 | 8/1994 | Unger . |
| 5,585,112 | 12/1996 | Unger et al. . |
| 5,653,998 | 8/1997 | Hamann et al. . |

FOREIGN PATENT DOCUMENTS

| | | |
|---|---|---|
| 2513797 | 7/1987 | (DE) . |
| 3940389 | 6/1991 | (DE) . |
| 4132677 | 4/1993 | (DE) . |
| 4411533 | 4/1995 | (DE) . |
| 0 357 163 | 8/1989 | (EP) . |
| EP 0 370 637 | 5/1990 | (EP) . |
| 0 523 315 | 1/1993 | (EP) . |
| 85/00011 | 1/1985 | (WO) . |
| 92/11052 | 7/1992 | (WO) . |
| 95/27438 | 10/1995 | (WO) . |
| 96/391197 | 12/1996 | (WO) . |
| 96/39197 | 12/1996 | (WO) . |
| 96/41647 | 12/1996 | (WO) . |

OTHER PUBLICATIONS

John C. Krantz, Jr. et al., "Current Comment: A Note on the Intarvenous Use of Anesthetic Emulsions in Animals and Man with Special Reference to Methoxyflurane" *Anesthesiology*, vol. 22, pp. 491–492 (1961.

John C. Krantz, Jr. et al., "Anesthesia LXIV: The Intravenous Administration of Methoxyflurane (Penthrane) Emulsions in Animals and Man" *Anesth. Analg.*, vol. 41, pp. 257–262 (1962).

Helmut F. Cascorbi, M.D., Ph.D., et al., "Hazards of Methoxyflurane Emulsions in Man", "Hazards of Methoxyflurane Emulsions in Man", *Anesth. Analg.* vol. 47, pp. 557–559 (1968).

Kadhim N. Salman, Ph.D., et al, "Intravenous Administration of a New Volatile Anesthetic, 2,2–Dichloro–1,1–Diflurooethyl Methyl Sulfide, in Dogs and Monkeys", "Intravenous Administration of a New Volatile Anesthetic . . . ", *Am. J. Vet. Res.* vol. 29, pp. 165–172 91968).

J. Chem. Phys. 90 (11), Jun. 1, 1989, "Solubility of xenon in 45 organic solvents including cycloalkanes, acids, and alkanals: Experiment and theory", Gerlad L. Pollack et al.

Anesth Analg, 1996, 82, pp. 103–107, "A Pilot Study of the Effects of a Perflubron Emulsion, AF 0104, on Mixed Venour Oxygen Tension in Anesthetized Surgical Patients", Joyce A. Wahr, M.D. et al.

Infusiontherapie 10: pp. 108–117 (Mar. 1983), "Allgemeine Charakteristika und Fragen zur Galenik von Fettemulsionen", G. Kleinberger et al.

Der Spiegel 15/1996, pp. 196–198, "Abstieg ins Unbewusste".

Wahr et al., "A pilot Study of the Effects of a Perfluron Emulsion, AF0104, on mixed venous oxygen tensionin Anesthetized Surgicasl Patients,"Anexth. Analg. 82:103–107 (1996).

Der Spiegel 15/1996, S. 196–198.

Pschyrembel, Klinisches Worterbuch, Walter de Gruyter, Berlin–New York 1977, p. 48.

B. Biber et al., "Intravenous Infusion of Halothane dissolved in fat. Haemodynamic effects in dogs," Acta Anaesthesiol Scand 1984, 28, pp. 385–389.

B. Lachmann et al., "Safety and efficacy of xenon in routine use of an inhalational anaesthetic", The Lancet, Vol. 335 (Jun. 16, 1990), pp. 1413–1415.

H. Luttropp et al., "Left ventricular performance and cerebral haemodynamics during xenon anaesthesia", Anaesthesia, 1993, vol. 48, pp. 1045–1049.

F. Giunta et al., "Xenon: a review of its anaesthetic and pharmacological properties", Applied Cardiopulmonary Pathophysiology OO: 1–9, 1996.

Ullmanns Encyklopädie der technischen Chemie, 4. ed., vol. 17, Chapter "Narkosemittel", Verlag Chemie, Weinheim–New York 1979; pp. 135–141.

S. Schraag und M. Georgieff, "Intravenös Anasthesie–Aktuelle Aspekte", Anasthesiol Intensivmed. Notfallmed. Schmerzther. 1995; 30:469–478; Georg Theieme Verlag Stuttgart–New York.

Rompo Chemie Lexikon (paperback–edition), vol. 5, Georg Thieme Verlag, Stuttgart 1995, "Propofol", pp. 3639–3640.

*Primary Examiner*—Carlos A. Azpuru

(57) ABSTRACT

A preparation is described which contains a lipophilic gas with a pharmacological action in dissolved or dispersed form. This preparation is particularly suitable for inducing anaesthesia.

16 Claims, No Drawings

MEDICINAL PREPARATION CONTAINING A LIPOPHILIC INERT GAS

The invention relates to a liquid preparation containing a lipophilic inert gas in a pharmacologically effective concentration.

Lipophilic inert gases are inert gases which have a degree of solubility in fat. This is expressed for example as an oil/gas partition coefficient of more than about 0.05 (krypton, 0.5; argon, 0.15; xenon, 1.9). Typically an oil such as n-octanol or olive oil is employed to measure such a coefficient. Alternatively lipophilicity of the inert gases may be defined with reference to the so-called Ostwald solubility (cf. Gerald L. Pollack et al. in J.Chem.Phys. 90 (11), 1989, "Solubility of xenon in 45 organic solvents including cycloalkanes, acids, and alkanals: experiment and theory"). The Ostwald solubility is the ratio of the concentration of dissolved gas molecules in a liquid solvent to their concentration in the gas phase at equilibrium. Thus the Ostwald solubility at 25° C. for xenon is about 4.8 in n-hexane. Accordingly the term lipophilic here defines a gas or a gas mixture (under standard conditions) having an Ostwald solubility of greater than about 0.2 in n-hexane at 25° C.

Pharmacologically or pharmaceutically effective is understood here as meaning a concentration in the liquid preparation which is capable of acting as a sedative, anaesthetic, analgesic, anti-inflammatory or muscle relaxant in a patient.

Xenon is being discussed inter alia as an inhalation anaesthetic because this inert gas has an anaesthetizing and analgesic action. As xenon is very expensive, its use as an inhalation anaesthetic involves a high consumption and treatment with a gas is also technically very expensive, anaesthesia with xenon has not been widely accepted. However, because of the obvious advantages of xenon gas compared with other gaseous anaesthetics, attempts are being made to facilitate the large-scale use of xenon, either by obtaining this gas in a simpler and less expensive way or by recovering it from the exhaled air.

Xenon is a colourless, odourless and tasteless monoatomic inert gas of atomic number 54. Xenon is five times denser than air. Naturally occurring xenon also contains isotopes, for example the isotopes 124, 126, 128, 129, 130, 131, 132, 134 and 136. Synthetic isotopes, like xenon 114, xenon 133 and xenon 142, are known as well. These isotopes disintegrate with half-lives of between 1.2 seconds and about 40 days. The present invention does not address such short living radioactive xenon isotopes.

When xenon is used as an inhalation anaesthetic, on the one hand very large amounts are required to achieve an anaesthetic action, and on the other hand the inspiratory concentration is limited to 70% or at most 79% in order to ensure that the patient is supplied with at least 21% of oxygen in the inhaled air. This allows a degree of anaesthesia and analgesia, although on its own this is not sufficient to ensure adequate general anaesthesia in a patient. It therefore has to be supplemented with additional sedatives or intravenous anaesthetics and analgesics. In the case of intraabdominal or intrathoracic interventions, it also has to be supplemented with muscle relaxants.

It is not known whether an attempt has ever been made to use a liquid preparation containing lipophilic inert gases as an injectable anaesthetic. It is also not known to use such preparations for other medicinal purposes as well, for example for analgesia or sedation.

DE-A-39 40 389 describes a therapeutic agent containing a gas in a concentration which is above its natural degree of saturation with the gas. Among the gases mentioned are atmospheric oxygen, ozone and an inert gas. Said publication explains in detail that the therapeutic agent is to be used for the purposes of emergency medicine and shock treatment, especially when this agent is administered to a patient by infusion as a blood substitute and oxygen transporter. Isotonic saline solution containing up to 40 mg/l of oxygen is indicated in particular as an agent according to the invention. Said publication gives no information about the possible activity of inert gases or the fields of use of an agent containing inert gases.

DE-A-16 67 926 discloses a pharmacologically acceptable salt solution containing a radioactive gas. The present invention does not address radioactive gases.

DE-C-41 00 782 describes aqueous ozone preparations which can be administered to a patient as infusion solutions. However, said publication emphasizes that ozone has certain algicidal, bactericidal, fungicidal, sporicidal and virucidal actions. It further mentions that ozone reacts in fractions of a second with the unsaturated fatty acids in the blood. Because ozone rapidly disintegrates, it is recommended to prepare the infusion solutions at the site of use.

As well as inhalation anaesthetics, injectable anaesthetics are described in the state of the art. Injectable anaesthetics are used either on their own (TIVA) or together with gaseous anaesthetics. Although one of the remarkable features of the intravenous anaesthetics in current use is an immediate onset of action, they regularly exhibit a host of disadvantages. It should be stressed that they develop only a weak pain inhibiting (analgetic) action, if any, and are difficult to control. Thus the advantage of a psychic protection of the patient during the induction of anaesthesia, whereby the patient momentarily loses consciousness and is spared the face mask and the excitation stage, is offset by the disadvantage of the increased risk of anaesthesia. This risk principally derives from the fact that, once the anaesthetic has been injected, the anaesthetist can have effectively no further influence, so the course of the anaesthesia is determined only by the processes occurring in the organism—distribution, enzymatic degradation and inactivation, as well as elimination via the liver and kidney. Other disadvantages of the injectable anaesthetics in current use are side effects which are difficult to assess (for example drop in blood pressure, bradycardia, rigidity, allergic reaction) and in some cases serious contraindications. As known intravenous anaesthetics are frequently administered together with analgesics and muscle relaxants, the latter additionally modify the pharmacokinetics, particularly the half-life, to a considerable extent. Overall, this makes the controllability substantially more difficult.

Anaesthesia consists of hypnosis, analgesia and muscle relexation. However, there is no single intravenous substance, active as an anaesthetic, which can bring about these three components of anaesthesia effectively and safely. This aim is achieved by using active substance combinations. The currently known active substances have a mutually adverse effect as regards both the pharmacodynamics and the pharmacokinetics. In particular, there is an enhancement of side effects which can be not only undesirable but also dangerous in anaesthesia. In particular, these include pronounced effects on the heart and blood vessels and on the cardiovascular control mechanisms.

U.S. Pat. No. 4,622,219 has disclosed a local anaesthetic which can be administered intravenously. This injectable local anaesthetic contains microdroplets composed predominantly of vaporizable anaesthetics, for example methoxyflurane. However, this infusion solution is active exclusively as a local anaesthetic. General anaesthesia or the anaesthesia of a patient is neither described nor considered. It should be emphasized in this connection that methoxyflurane is about 440 times more active than gaseous inhalation anaesthetics like xenon (activity expressed as minimum alveolar concentration of anaesthetic at 1 atm (MAC); MAC values in % by volume: xenon, 71; methoxyflurane, 0.16).

There is consequently an appreciable need for an intravenous anaesthetic of high activity which does not exhibit said disadvantages.

Accordingly it is an object of the present invention to provide a liquid preparation which can be utilized for inducing anaesthesia, sedation, analgesia, and/or muscular relaxation.

A further object of the present invention is to provide a liquid preparation for inflammation therapy.

Another object of the present invention is the provision of an infusion agent for inducing or maintaining anaesthesia which overcomes all or some of the draw backs of the above described prior art.

Still another object of the invention relates to methods of treatment wherein a preparation will be parenterally administered to induce anaesthesia, sedation, analgesia and/or muscle relaxation. Thus, it is a general object of the present invention to provide novel methods of inducing anaesthesia, sedation, analgesia and/or muscular relaxation, and inflammation therapy.

In comprehensive terms, the invention provides a liquid preparation containing a lipophilic inert gas in dissolved or dispersed form.

In particular the present invention contemplates to utilize gases as such or mixtures thereof, such as xenon and/or krypton.

As will be discussed in more detail below, the preparations according to the present invention surprisingly have a systemic effect on the central nervous system.

In contrast to the physiological limitations of using inert gases as inhalation anaesthetics, as described in connection with xenon, the anaesthesiological possibilities for the intravenous administration of a lipophilic inert gas, for example xenon, are completely different. They permit hitherto unrecognized improvements and, in particular, safety for the patient. Even preparations containing very small amounts of xenon produce pronounced anaesthesia and analgesia. This is totally surprising. It has further been established that xenon does not have an adverse effect on the cardiac musculature. Xenon also exerts no effect on the cardiac conduction system. Thus the inert gas has no adverse effect at all on the cardiac rhythm or the myocardial contractility. The preparation according to the invention makes it possible to achieve both complete anaesthesia and analgesia in a patient, which makes further supplementation with other intravenous sedatives, anaesthetics or analgesics superfluous. It is also possible to use doses which achieve central muscular relaxation, so supplementation with muscle relaxants also becomes superfluous. Thus, already during the induction of anaesthesia, a patient can be subjected to anaesthesia, analgesia and muscle relaxation by mono-intravenous anaesthesia with the lipophilic inert gas, so intubation can be carried out without problems. Further, problems have been reported with regard to the use of xenon as inhalation anaesthetic with patients with obstructive pulmonary diseases like asthma and others. The present invention also overcomes problems with such patients.

It has been found that the administration of a preparation according to the present invention as opposed to the use of xenon as inhalation anaesthetic reduces dose requirements and produces more rapid onset and recovery of anaesthetic effect. It seems that the liquid preparation of the present invention alters xenon disposition and possibly the intrinsic uptake and distribution of xenon to tissues. One possible explanation may be that the liquid preparations (i.e. emulsions) restrict the xenon within the vascular space and decrease the volume of distribution. An alternative explanation of the effect in providing xenon in the form of a liquid preparation could be that emulsion vesicles of the liquid preparation of the present invention may diminish the extent of first-pass pulmonary uptake, accelerate pulmonary transit after intravenous administration, or both.

The invention also opens up new possibilities for the supplementation of intravenous medication, e.g. if a patient is additionally required to be sedated. This includes, inter alia, the forms of renal replacement therapy, such as haemofiltration, haemodiafiltration and haemodialysis, extracorporal membrane oxygenation or extracorporal $CO_2$ elimination, and heart-lung machines. In such cases, xenon can be administered to a patient as part of these therapeutic procedures. The preparation according to the invention can then be infused as well and/or the blood is enriched with xenon.

According to the invention, liquid preparations are provided which, by virtue of a certain lipophilicity, can easily take up a fat-soluble gas like the abovementioned xenon or krypton.

Blood substitutes, especially perfluorocarbon emulsions (e.g. Perflubron), can be regarded as examples of such liquids.

Perfluorocarbons can be administered intrapulmonarily, inter alia, so when they are loaded with xenon they can also be used on the one hand to treat acute lung damage, but on the other hand also to induce anaesthesia, sedation and/or analgesia on the basis of the pharmacological action of xenon. The intrapulmonary administration of perfluorocarbon together with xenon for partial liquid ventilation and additionally for anaesthesia or else alleviation of pain is a novel approach to the treatment of severe respiratory crises. It reopens collapsed, atelectatic areas of the lung which cannot be reached by conventional therapy, thereby preparing these areas of the lung for renewed gas exchange.

Perfluorocarbons can also be administered intravenously, so a preparation according to the invention which is based on perfluorocarbons can be used for i.v. anaesthesia by means of xenon. However, perfluorocarbons also have a loading capacity for oxygen, offering the possibility of intravenously administering perfluorocarbons which are simultaneously laden with oxygen. Thus it is possible not only to induce anaesthesia but also to induce anaesthesia and supply (supplementary) oxygen. Difficult intubations of any kind can therefore be carried out with a hitherto unknown degree of patient safety, namely the avoidance of hypoxia.

It is generally known that a large number of gases have a high solubility in perfluorocarbon compounds. A perfluorocarbon emulsion according to the invention consists for example of up to 90% (weight/volume) of perflubron ($C_8F_{17}$). Emulsifiers, for example phospholipids from chicken egg yolk, are additionally required. These emulsions which can be loaded according to the invention with xenon have been reported for example by J. A. Wahr et al. in Anesth. Analg. 1996, 82, 103–7.

Suitable fluorocarbon emulsions preferably comprise 20% w/v to 125% w/v of a highly fluorinated hydrocarbon compound, for example polyfluorinated bisalkylethenes, cyclic fluorocarbon compounds like fluorodecalin or perfluorodecalin, fluorinated adamantane, or perfluorinated amines like fluorinated tripropylamine and fluorinated tributylamine. It is also possible to use monobrominated perfluorocarbons, for example 1-bromoheptadecafluorooctane ($C_8F_{17}Br$), 1-bromopentadecafluoroheptane ($C_7F_{15}Br$) and 1-bromotridecafluorohexane ($C_6F_{13}Br$). Other compounds can also be used, including perfluoroalkylated ethers or polyethers, e.g. $(CF_3)_2CFO(CF_2CF_2)_2OCF(CF_3)_2$, $(CF_3)_2CFO\!-\!(CF_2CF_2)_3OCF(CF_3)$, $(CF_3)_2CFO(CF_2CF_2)_2F$, $(CF_3)_2CFO(CF_2CF_2)_3F$ and $(C_6F_{13})_2O$.

Chlorinated derivatives of the abovementioned perfluorocarbons can also be used.

The loading capacity of the abovementioned perfluorocarbon preparation is considerable. Xenon loads of e.g. 1 to 10 ml/ml have been achieved by the simplest means. For example, these preparations can be loaded with inert gas simply by having the gas passed through them. The volume of the gas to be included in the liquid preparation of the present invention may be measured by simple methods known to the skilled person, such as gravimetric measurements or other analytical means, or control measurements with for instance radioactive xenon (i.e. Xenon 133) as described by Gerald L. Pollack (see above).

The invention also provides (fatty) emulsions containing the lipophilic inert gas dissolved or dispersed in the lipid phase.

It has been found that xenon can be added to an (fatty) emulsion in appreciable amounts. Thus, even by the simplest means, xenon can be dissolved or dispersed in concentrations of 0.2 to 10 ml or more per ml of emulsion (concentrations relate to standard conditions, i.e. 20° C. and normal pressure). The xenon concentration depends on a large number of factors, especially the concentration of the fat or lipophilic substance. As a rule the preparations according to the invention will be "loaded" with xenon up to the saturation limit. However, it is also possible for very small concentrations to be present, provided, for example, that a pharmacological activity can still be observed on intravenous administration. In the case of a 10% fatty emulsion, it is easily possible to reach xenon concentrations of 0.3 to 2 ml of xenon per ml of emulsion. It may be of course also possible to reach higher values, e.g. 3, 4, 5, 6 or 7 ml of xenon per ml of emulsion. These fatty emulsions are sufficiently stable, at least in gas-tight containers, for the xenon not to be released as a gas over conventional storage periods. It is quite surprising that these emulsions can be hyperbaric loaded to high concentrations of xenon in the emulsion, and still these emulsions are sufficiently stable.

A large number of documents in the state of the art describe contrast media containing a gas, especially for ultrasound studies or nuclear magnetic resonance spectrometry. An essential feature of such contrast media is that a separate phase is formed which is made up of very small gas bubbles (or even gas-filled balloons) (cf. inter alia WO-A-96/39197, U.S. Pat. No. 5,088,499, U.S. Pat. No. 5,334,381, WO-A-96/41647). A large number of gases are proposed, including especially air, nitrogen, carbon dioxide, oxygen and also inert gases in general (i.e. helium, argon, xenon and neon). Only EP-B-0 357 163 discloses in definite terms that xenon-containing media in particular can be used as X-ray contrast media. Here again it is emphasized that the injectable solution must contain gas bubbles. Further, WO-A-95/27438 discloses the use of xenon in a method of imaging of a noble gas by nuclear magnetic resonance. However, at no point is there any suggestion that xenon has an analgesic or anaesthetic action when used as a contrast medium or for spectrometry. In fact, such an action would also be undesirable. Moreover, the gas concentration in contrast media is also so small that the limiting concentration for a pharmacological action is not reached. Therefore, contrast media as such or formulations to be used in spectrometry are not claimed in the present patent application.

The lipid phase of the preparation, which takes up the gas, i.e. which can dissolve and/or disperse the gas, is formed mainly of so-called fats, said fats being essentially esters of long-chain and medium-chain fatty acids. Such fatty acids, saturated or unsaturated, contain 8 to 20 carbon atoms. However, it is also possible to use omega-3 or omega-6 fatty acids, which can contain up to 30 carbon atoms. Suitable esterified fatty acids are especially plant oils, e.g. cottonseed oil, soya bean oil and thistle oil, fish oil and the like. The major constituent of these naturally occurring oils are fatty acid triglycerides. Preparations in the form of so-called oil-in-water emulsions are of particular importance, the proportion of fat in the emulsion conventionally being 5 to 30% by weight, preferably 10 to 20% by weight. As a rule, however, an emulsifier is present together with the fat, proven emulsifiers being soya phosphatides, gelatin or egg phosphatide. Such emulsions can be prepared by emulsifying the water-immiscible oil with water in the presence of the emulsifier, which is normally a surface-active agent. Other polar solvents can also be present with the water, examples being ethanol and glycerol (propylene glycol, hexylene glycol, polyethylene glycol, glycol monoethers, a water-miscible ester, etc.). The inert gas can already have been incorporated into the lipid phase in a previous process step. In the simplest case, however, the preprepared emulsion is loaded with the xenon. This can take place at various temperatures, for example at temperatures from 1° C. to room temperature. It is occasionally useful here to apply a pressure, for example of up to 8 atmospheres or more, to the vessel containing the emulsion.

According to the invention, it is possible to use fatty emulsions such as those employed in intravenous feeding. These fatty emulsions consist essentially of a suitable fatty base (soya bean oil or sunflower seed oil) and a well-tolerated emulsifier (phosphatides). Fatty emulsions in general use are Intralipid®, Intrafat®, Lipofundin® S and Liposyn®. More detailed information on these fatty emulsions can be found in G. Kleinberger and H. Pamperl, Infusionstherapie, 108–117 (1983) 3. The fatty emulsions generally also contain additives which make the osmolarity of the aqueous phase, surrounding the fatty phase present in the form of liposomes, isotonic with the blood. Glycerol and/or xylitol can be used for this purpose. Furthermore, it is frequently useful to add an antioxidant to the fatty emulsion in order to prevent oxidation of the unsaturated fatty acids. Vitamin E (DL-tocopherol), in particular, is suitable for this purpose.

So-called liposomes, which can be formed from the abovementioned triglycerides but also generally from so-called phospholipid molecules, are particularly advantageous as the lipid phase, especially in the case of an oil-in-water emulsion. These phospholipid molecules generally consist of a water-soluble part, which is formed of at least one phosphate group, and a lipid part, which is derived from a fatty acid or fatty acid ester.

U.S. Pat. No. 5,334,381 illustrates in detail how liposomes can be loaded with gas. In very general terms, a device is filled with the liposomes, i.e. with an oil-in-water emulsion, and the device is then pressurized with the gas inside. The temperature can be reduced to as low as 1° C. in this process. The gas gradually dissolves under pressure and passes into the liposomes. Small gas bubbles may then form when the pressure is released, but these are now encapsulated by the liposomes. It is thus possible in practice to keep xenon gas or other gases, for example, in a fatty emulsion under hyperbaric conditions. Such preparations can also be used according to the invention, provided that a separate gas phase does not form outside the liposomes and on condition that the desired pharmacological action takes place.

The lipids which form the liposomes can be of natural or synthetic origin. Examples of such materials are cholesterol, phosphatidylcholine, phosphatidylethanolamine, phosphatidylserine, phosphatidylglycerol, phosphatidylinositol, sphingomyelin, glycosphingolipids, glucolipids, glycolipids, etc. The surface of the liposomes can moreover be modified by a polymer, for example by polyethylene glycol.

The preparations according to the invention thus have a large number of advantages. Thus it was possible to observe that, after injection with a preparation according to the invention, a virtually immediate anaesthetic effect took place which, in contrast to all known injectable anaesthetics, could easily be controlled. However, the agent according to the invention has not only an anaesthetic action but also a simultaneous analgesic action and, on waking, a euphoretic action. The elimination from the body depends exclusively on the respiration. Furthermore, with an intravenous anaesthetic, the xenon concentration can easily be measured in the exhaled air. The control of anaesthesia which can be achieved in this way was not possible hitherto with conventional intravenous anaesthetics.

The invention thus provides medicinal liquid preparations containing a lipophilic inert gas in a pharmacologically effective concentration with the proviso that preparations used as contrast media or for spectrometry are excluded. Pharmacologically effective is understood here as meaning anaesthetic (including subanaesthetic), analgesic, muscle relaxing, sedative and/or anti-inflammatory. In particular the pharmacological effectiveness of the present invention may relate to the systemic action on the central nervous system.

To achieve a subanaesthetic action, for example, the xenon load in the medicinal preparation may be about 0.2 to 0.3 ml of xenon per ml of emulsion. This means that an analgesic and/or sedative action may be assured for preparations with a xenon content of at least 0.2 ml/ml emulsion. An anti-inflammatory action may be already observed at 0.1 ml/ml emulsion. It was observed that, with continuous infusion over 30 sec, 20 ml of an emulsion containing 0.3 ml of Xe per ml of emulsion produce a subanaesthetic condition in a patient weighing about 85 kg. When working with a highly laden perfluorocarbon emulsion containing 2 to 4 ml of xenon per ml of emulsion, for example, 20 ml of this emulsion may be infused over 30 sec, for example, in order to induce anaesthesia. An infusion rate of at least 7.5 ml/min may be sufficient to maintain the anaesthesia. A total of 470 ml of emulsion would thus be used for a 1-hour operation. With a xenon content of 3 ml of xenon per ml of emulsion, this corresponds to a xenon volume of 1410 ml, i.e. a fraction of the xenon consumed in inhalation anaesthesia (based on a body weight of 85 kg, this would be a consumption of 16.6 ml per kg in one hour).

Anyhow, a skilled person may easily determine the effective xenon concentration by trial and error. As has been pointed out before the presence of an emulsion or a lipid phase in the liquid preparation according to the invention has an effect on the pharmacological action. Thus, the above given concentration limits may be operative for emulsions containing 10 to 40% (weight/volume) lipid or fluorocarbon emulsions. However, the present invention also contemplates emulsions comprising more than 40% w/v and up to 125% w/v of for instance hydrocarbon compounds; e.g. fluorinated and/or chlorinated derivatives thereof. With such emulsions the loading capacity of the liquid preparation may be well above the above given limits. On the other hand, as described above, the emulsions as such impact the efficacy of the xenon in the liquid preparation. Thus, for certain indications the required xenon concentration may be drastically lower.

The preparation according to the invention can thus be combined with any known inhalation anaesthetic, i.e. an i.v. administration is accompanied by inhalation anaesthesia. In the combined use with laughing gas or xenon and/or with other anaesthetics like halothane, diethyl ether, sevoflurane, desflurane, isoflurane, Ethrane etc., the concentration or amount of inhalation anaesthetic used can be reduced under certain circumstances.

It is furthermore possible, and under certain circumstances also advantageous, to include another pharmacologically active agent in the preparation in addition to the inert gas. This can be an intravenous sedative or anaesthetic, for example. Depending on whether this agent is water-soluble or fat-soluble, it is then present in the aqueous phase or the lipid phase together with the xenon. 2,6-Diisopropylphenol, which is an effective anaesthetic (for example 1.5–20 mg/ml), is found to be particularly suitable for this purpose. Etomidate in concentrations of 0.1–2 mg/ml (Hypnomidate®, an imidazole-5-carboxylic acid derivative) is also suitable. Using dissolved xenon in addition to the other anaesthetic makes it possible to lower the concentration of e.g. diisopropylphenol or etomidate which is necessary for anaesthetization. Thus, for example, 1 ml of fatty emulsion according to the invention (containing about 0.1 g of fat per ml of emulsion) can contain 2.5–20 mg of 2,6-diisopropylphenol, i.e. for example 2.5, 5.0, 7.5, 10, 15 or 20 mg, in addition to the xenon.

In very general terms, the substance with an anaesthetic, analgesic or sedative action which is present together with the xenon can be another anaesthetic, an analgesic, a muscle relaxant or a sedative. Examples of other suitable anaesthetics are barbiturates (barbital, phenobarbital, pentobarbital, secobarbital, hexobarbital and thiopental, inter alia) in general, and opioids. Known analgesics are, inter alia, compounds of the morphine type, e.g. hydromorphone, oxymorphone, codeine, hydrocodone, thebacon and heroin. It is also possible to use synthetic derivatives of morphine, e.g. pethidine, levomethadone, dextromoramide, pentazocine, fentanyl and alfentanil. It is also possible to use less potent analgesics such as anthranilic acid derivatives (flufenamic acid, mefenamic acid), acrylic acid derivatives (diclofenac, tolmetin, zomepirac), arylpropionic acid derivatives (ibuprofen, naproxen, phenoprofen, ketoprofen) and indoleacetic or indenacetic acid derivatives (indometacin, sulindac). The muscle relaxants used can be central muscle relaxants, for example baclofen, carisoprodol, chlordiazepoxide, chlormezanone, chloroxazone, dantrolene, diazepam, phenyramidol, meprobamate, phenprobamate and orphenadrine. Sedatives which can be used according to the invention are, inter alia, benzodiazepine derivatives such as triazolam, lormetazeban, clotiazepam, flurazepam, nitrazepam and flunitrazepam.

A preparation according to the invention can consequently serve several purposes:
a) intravenous induction of anaesthesia (optionally with 2,6-diisopropylphenol or etomidate as a supporting component);
b) supplementary intravenous administration in parallel with inhalation anaesthesia with xenon or another gas (e.g.

laughing gas or desflurane), it being possible considerably to reduce the amount of gas to be used overall;

c) maintenance of anaesthesia over a prolonged period, the inert gas-containing preparation optionally being administered only as a supplement together with 2,6-diisopropylphenol or etomidate, for example; as the concentration of diisopropylphenol, for example, can be considerably reduced here, prolonged anaesthesia virtually free of side effects becomes possible;

d) because xenon has an analgesic action, it is possible, by combining it with an inhalation anaesthetic or an intravenous anaesthetic, appreciably to reduce or totally dispense with a supplementary analgesic;

e) intravenous xenon preparations, whether or not combined with inhalation or intravenous anaesthetics, reduce the need for muscle relaxants up to the point where they can be totally dispensed with.

As is apparent from the above remarks, the invention is not restricted to anaesthesia as the field of use. The term anaesthesia here includes both the induction and the maintenance of anaesthesia. Additionally, however, the preparations according to the invention also have a pain eliminating action, which can become significant in conjunction with anaesthesia. Under certain circumstances, however, the elimination of pain, for example acute and chronic pain therapy, also comes to the fore, a degree of additional sub-anaesthetic or sedative action often being desirable. Intravenous administration in a subanaesthetic dose over a long period of time (1 h to several days) effects an increased pain inhibiting action. One particular field of use of a preparation according to the invention as an anaesthetic is emergency medicine. This frequently demands especially short waking phases following deep painless anaesthesia. Another example is the acute treatment of a cardiac infarction. In this case the preparation according to the invention serves to lower the sympathetic tone and alleviate pain. Thus the agent according to the invention can also be used very generally in inflammation and pain therapy. A further possibility here, inter alia, is topical use of the agent according to the invention.

It is also possible to consider ointments and creams (fatty emulsion or liposomes) and the like, which can be applied for example to damaged tissue. These preparations can also be sprayed into cavities or joints in order to effect a pharmacological action.

Ointments or creams according to the invention are particularly suitable for the local alleviation of pain. Here the ointment is applied to the area to be treated and is optionally provided with an airtight wound closure. The invention can consequently also be put into effect by means of a plaster which carries the preparation according to the invention on the side to be applied to the wound, and takes the form of a conventional plaster covering, which is optionally of airtight design, on the other side.

In the broadest sense, the invention can thus be understood as a liquid or gel-like preparation containing the inert gas in dissolved or dispersed form. As demonstrated here using a fatty emulsion as an example, the liquid or gel-like preparation according to the invention is characterized in that it contains the gas with the pharmacological action dissolved in a finely divided, separate phase. As a rule, this separate phase is the disperse phase of a dispersion or emulsion. However, the separate phase containing the gas can also be the continuous phase. The preparations according to the invention are generally composed in such a way that the disperse phase as such has the property of dissolving the gas. As regards the lipophilic inert gas used, one possibility is therefore to have a fatty emulsion with separate, very small fat droplets or liposomes, which then contain the inert gas in dissolved form. Very generally, however, it should be stated that the preparations according to the invention are preferably emulsions in which the disperse phase normally contains the active gas.

A further embodiment of the present invention is a method for inducing anaesthesia, sedation, analgesia, muscular relaxation and for inflammation therapy. In the course of such treatment a liquid preparation is administered to a patient usually by the parenteral route. In addition, the present invention relates to a method of maintaining anaesthesia by adimininstration of the above described liquid preparation. In such a method the adiministration of the liquid preparation according to the present invention ensures rapid onset of the described effects. A particular advantage of any of the above described methods according to the present invention lies in the fact that the liquid preparation can be administered over long time intervals, such as several minutes and hours, without causing e.g. inflammatory side effects.

Experimental section

Fatty emulsions

The commercially available Intralipid preparations (obtainable from Pharmacia & Upjohn GmbH, Erlangen) were used as fatty emulsions in the following Examples. These emulsions consist essentially of soya bean oil, 3-sn-phosphatidylcholine (from chicken egg yolk) and glycerol. An Intralipid® 10 fatty emulsion, for example, has the following composition:

| | |
|---|---|
| Soya bean oil | 100 g |
| (3-sn-Phosphatidyl) choline from chicken egg yolk | 6 g |
| Glycerol | 22.0 g |
| Water for injections ad | 1000 ml |

Adjusted to pH 8.0 with sodium hydroxide.
Energy value/l: 4600 kJ (1100 kcal)
Osmolarity: 260 mOsm/l An Intralipid ® 20 fatty emulsion, for example, has the following composition:

| | |
|---|---|
| Soya bean oil | 200 g |
| (3-sn-Phosphatidyl)choline from chicken egg yolk | 12 g |
| Glycerol | 22.0 g |
| Water for injections ad | 1000 ml |

Adjusted to pH 8.0 with sodium hydroxide.
Energy value/l: 8400 kJ (2000 kcal)
Osmolarity: 270 mOsm/l Loading of perfluorcarbon emulsions with xenon A series of perfluorocarbon emulsions were prepared or purchased and loaded with xenon. The activity of the preparations was verified on an animal model (rabbit). All the emulsions were used in the same way as the Intralipid preparations described above, i.e. the experimental animal was quickly anaesthetized by an injection in the ear (about 1 ml).

Each of the emulsions was placed in a beaker and loaded by having the xenon gas passed through it.

The following perfluorocarbon compounds were used: perfluorohexyloctane (1), perfluorodecalin (2), perflubron ($C_8F_{17}$) (3).

Emulsifiers, for example egg yolk lecithin (Lipoid E100 from Lipoid GmbH, Ludwigshafen), Pluronic PE6800 and Pluronic F68, were also used to prepare the emulsions.

It was established with all the emulsions that a perfluorocarbon emulsion of only 40% (weight/volume, i.e. weight of perfluorocarbon compound to volume of emulsion) could take up 1 to 4 ml of xenon per ml of emulsion.

Experimental animal studies

To demonstrate the efficacy of the preparations according to the invention, an experiment was performed on 24 pigs aged 14 to 16 weeks and weighing 36.4–43.6 kg. They were randomly divided into a total of 6 groups, which were anaesthetized either in conventional manner or by means of the emulsion according to the invention. In all the groups the anaesthesia was induced intravenously with a bolus injection of pentobarbitone (8 mg/kg body weight) and buprenorphine (0.01 mg/kg body weight). The anaesthesia was then continued by means of conventional inhalation anaesthetics (laughing gas or a xenon/oxygen mixture) or the intravenous administration of pentobarbitone and buprenorphine. In one group (comparative group) the anaesthesia was maintained by the intravenous administration of 2,6-diisopropylphenol (10 mg/1 ml emulsion). For maintenance of the anaesthesia, two groups of pigs (according to the invention), each containing four individuals, received an intravenous infusion of 1 ml/kg/h of a 10% by weight fatty emulsion according to the invention which had previously been saturated with xenon (about 0.3 ml of xenon per ml of emulsion). In group 2, 7.5 mg/kg body weight/h of 2,6-diisopropylphenol were additionally administered with the fatty emulsion.

The pigs underwent a surgical intervention (standard intervention: section of the left femoral artery) (identical in each group and for each experimental animal) and the adrenaline level, heart rate, arterial blood pressure and oxygen consumption were recorded. It was also established how much additional pentobarbitone needed to be administered in order to bring the analgesia and depth of anaesthesia to the required level in each group.

TABLE

| Group | Adrenaline pg/ml | Heart rate [min$^{-1}$] | Arterial blood pressure [mm Hg] | $\dot{V}O_2$ [ml/ min] | Pentobarbitone requirement mg/kg/min |
|---|---|---|---|---|---|
| Comparative group | 60 | 115 | 110 | 410 | 0.25 |
| | 134 | 120 | 105 | 391 | 0.36 |
| | 112 | 105 | 115 | 427 | 0.31 |
| | 85 | 98 | 101 | 386 | 0.42 |
| Group 1 | 38 | 112 | 112 | 341 | 0.09 |
| | 21 | 106 | 100 | 367 | 0.04 |
| | 16 | 95 | 104 | 348 | 0.11 |
| | 30 | 112 | 118 | 334 | 0.15 |
| Group 2 | 10 | 88 | 100 | 325 | — |
| | 23 | 100 | 85 | 346 | — |
| | 14 | 94 | 93 | 331 | — |
| | 8 | 104 | 87 | 354 | — |

Evaluation of the results pertaining to the groups which were anaesthetized in conventional manner (not tabulated here) showed that anaesthesia with a xenon/oxygen mixture was markedly superior to the other methods. Surprisingly, the two groups which had received an intravenous administration of a fatty emulsion according to the invention (group 1 and group 2) showed similarly favourable results, it even being possible to achieve significant improvements in the case of a combined administration together with 2,6-diisopropylphenol (group 2), as demonstrated by a lower adrenaline level (less stress) and no pentobarbitone requirement at all.

The values indicated in the Table show that the preparation according to the invention is superior to all the currently available intravenous anaesthetics, especially on account of the additional analgesic potency. Thus the pigs in group 1 (10% by weight fatty emulsion saturated with xenon) show, by comparison (cf. comparative group), markedly less stress (adrenaline level), a lower oxygen consumption ($VO_2$) and a lower pentobarbitone requirement (i.e. better anaesthesia). The difference relative to intravenous anaesthetics according to the state of the art is even more clearly apparent when the results in group 2 (10% fatty emulsion with 2,6-diisopropylphenol and enriched with xenon) are compared with the comparative group. This shows not only markedly reduced stress (adrenaline level). With a markedly reduced heart rate and lower arterial blood pressure, coupled with a lower oxygen requirement, it was possible to dispense with the administration of additional amounts of pentobarbitone.

The use of perfluorocarbon preparations was studied on another group (4 pigs of 31.4 to 39.8 kg body weight). A 40% perfluorocarbon emulsion with a xenon content of 2.1 ml of xenon per ml of emulsion was used on this experimental group. For induction and intubation, the pigs received 20 ml of the emulsion intravenously over 20 sec (corresponding to 1.34 ml xenon/kg body weight). After intubation and respiration, xenon was continuously infused intravenously over 30 min, the experimental animals thereby receiving a total of 75 ml of emulsion (corresponding to 10 ml xenon kg$^{-1}$h$^{-1}$).

The following Table indicates the experimental results for the adrenaline level, the heart rate, the arterial blood pressure and the oxygen consumption. The results show that, by increasing the xenon load and infusion rates (over 5 ml/kg/h), complete anaesthesia can be effected using only the agent according to the invention. Overall, it is even established that the oxygen consumption ($VO_2$) is lower and the anaesthesia (adrenaline level and heart rate) is less stressed.

| Adrenaline [pg/ml] | Heart rate [min$^{-1}$] | Arterial blood pressure [mm Hg] | $\dot{V}O_2$ [ml/min] |
|---|---|---|---|
| 8 | 90 | 101 | 301 |
| 6 | 87 | 96 | 320 |
| 10 | 94 | 98 | 308 |
| 5 | 100 | 106 | 316 |

Experiment on one's own body

The inventor of the present invention conducted an experiment with the preparation according to the invention to determine the efficacy of said preparation. In this experiment a fatty emulsion of Intralipid®10 fatty emulsion was loaded with xenon as described above. As determined by gravimetric methods said preparation contained about 1.5 ml xenon in 1 ml emulsion. Anaesthesia was induced by injecting 20 ml of said emulsion over a time period of about 30 sec. An immediate onset of anaesthesia was observed. Thereafter the anaesthesia was maintained by infusion at a rate of about 40 ml/h of said emulsion. After about 10 min the administration of the liquid preparation was stopped. About 30 sec thereafter the inventor regained consciousness and summoned his colleagues for a detailed discussion of the conducted experiment shortly thereafter. The inventor reported no dizziness or other side effects as usually observed after anaesthesia with well known anaesthetic agents of the prior art, such as 2,6-diisopropylphenol (propofol).

In none of the above experiments any acute or apparent toxicity was observed.

What is claimed is:

1. Liquid preparation for inducing and/or maintaining anaesthesia, comprising a lipophilic inert gas in a concentration effective as an anaesthetic.

2. Liquid preparation for inducing sedation, comprising a lipophilic inert gas in a concentration effective as a sedative.

3. Liquid preparation for inducing analgesia, comprising a lipophilic inert gas in a concentration effective as an analgesic.

4. Liquid preparation for inducing muscular relaxation, comprising a lipophilic inert gas in a concentration effective as a muscle relaxant.

5. Liquid preparation for inflammation therapy, comprising a lipophilic inert gas in a concentration effective as an anti-inflammatory.

6. Liquid preparation according to claim 1, comprising xenon in dissolved or dispersed form.

7. Preparation according to claim 1 which is in the form of a perfluorocarbon emulsion.

8. Preparation according to claim 1 which is in the form of a fatty emulsion including an oil-in-water emulsion or dispersion and a liposomal emulsion.

9. Preparation according to claim 1 in which another pharmacological agent is additionally present in dissolved form.

10. Preparation according to claim 9 wherein the additional pharmacologically active agent is an intravenous anaesthetic, analgesic, sedative or muscle relaxant.

11. Preparation according to claim 10 wherein the additional pharmacologically active agent is 2,6-diisopropylphenol, etomidate or a derivative thereof.

12. Preparation according to claim 10 wherein the additional pharmacologically active agent is fentanyl or alfentanil.

13. Infusion agent for anaesthesia, which comprises a preparation according to claim 1.

14. Method for inducing and/or maintaining anaesthesia wherein a liquid preparation comprising a lipophilic inert gas in a concentration effective as an anaesthetic is administered to a patient in need of anaesthesia.

15. Method for inducing sedation wherein a liquid preparation comprising a lipophilic inert gas in a concentration effective as a sedative is administered to a patient in need of sedation.

16. Method for inducing and/or maintaining analgesia wherein a liquid preparation comprising a lipophilic inert gas in a concentration effective as an analgetic is administered to a patient in need of anaesthesia.

* * * * *